United States Patent [19]

Inamoto et al.

[11] 4,277,473
[45] Jul. 7, 1981

[54] 4-HOMOISOTWISTANE-AMINOACID AMIDES

[75] Inventors: Yoshiaki Inamoto, Utsunomiya; Motoyoshi Osugi; Eiji Kashihara, both of Wakayama, all of Japan

[73] Assignees: Kao Soap Co., Ltd., Tokyo; Sumitomo Chemical Industries Ltd., Osaka, both of Japan

[21] Appl. No.: 102,702

[22] Filed: Dec. 12, 1979

[30] Foreign Application Priority Data

Dec. 21, 1978 [JP] Japan ............... 53-159540

[51] Int. Cl.$^3$ ............... C07C 103/50; C07C 103/68; A61K 31/16
[52] U.S. Cl. ............... 424/248.54; 424/267; 424/274; 260/326.39; 542/415; 544/154; 544/155; 546/203; 564/164; 564/165; 564/188; 564/189; 564/191; 564/193
[58] Field of Search ........... 260/563 P, 561 A, 557 R, 260/555 A, 326.39; 542/415; 546/203; 544/154, 155; 424/274, 267, 248.54; 564/164, 161, 193, 188, 189, 191

[56] References Cited

U.S. PATENT DOCUMENTS

| | | | |
|---|---|---|---|
| 3,919,313 | 11/1975 | Villani | 260/561 A |
| 4,157,342 | 6/1979 | Inamoto | 260/563 P |

FOREIGN PATENT DOCUMENTS 1006885 10/1965 United Kingdom.

OTHER PUBLICATIONS

Aigami et al., J. Med. Chem. 19 (1976) pp. 536–540.
Aldrich et al., J. Med. Chem. 14 (1971) pp. 535–543.

*Primary Examiner*—Arthur P. Demers
*Attorney, Agent, or Firm*—Blanchard, Flynn, Thiel, Boutell & Tanis

[57] ABSTRACT

Compounds having the formula

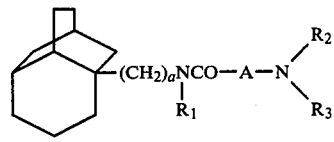

wherein a is 0 or 1, $R_1$ is hydrogen or lower alkyl, A is lower alkylene or lower alkylidene, and $R_2$ and $R_3$, which can be the same or different, are hydrogen, lower alkyl, cycloalkyl, benzyl or substituted benzyl, or

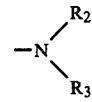

is a saturated heterocyclic ring, and acid addition salts thereof, possess anti-viral activity and reduced activity on the central nervous system.

9 Claims, No Drawings

4-HOMOISOTWISTANE-AMINOACID AMIDES

The present invention relates to aminoacid amides of amine derivatives of tricycloundecane and acid addition salts thereof. More particularly, the present invention relates to aminoacid amides of amine derivatives of 4-homoisotwistane (tricyclo[5,3.1.0³,⁸]undecane) represented by the following general formula (I) and acid addition salts thereof:

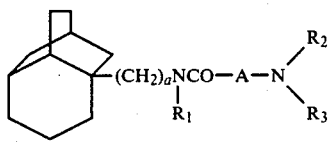

wherein a is 0 or 1, $R_1$ stands for a hydrogen atom or a lower alkyl group, A stands for a lower alkylene or lower alkylidene group, and $R_2$ and $R_3$, which can be the same or different, stand for a hydrogen atom, a lower alkyl group, a cycloalkyl group, a benzyl group or a substituted benzyl group, or they form a saturated heterocyclic ring together with the adjacent nitrogen atom.

It is known that some cage compounds have an anti-RNA-viral activity, but cage compounds having an anti-DNA-viral activity are scarcely known and only tromantadine is known to have such an activity (Japanese Patent Publication No. 32526/74). Recently, 3-amino-4-homoisotwistane (3-aminotricyclo[5.3.1.0³,⁸]undecane) hydrochloride and 3-aminomethyl-4-homoisotwistane (3-aminomethyltricyclo[5.3.1.0³,⁸]undecane) hydrochloride have been reported as being novel cage compounds [Aigami et al., Journal of Medicinal Chemistry, 19, page 536 (1976), and Japanese Patent Application Laid-Open Specification Nos. 5755/77, No. 19647/77 and No. 18830/77]. However, it is only known that these compounds are effective against the Newcastle disease virus, which belongs to the RNA viruses, in the chicken embryo cell in vitro test system.

Amantadine (1-aminoadamantane hydrochloride) has been practically used as an anti-influenza agent, but because it has side effects on the central nervous system, administration of it to patients having central nervous system diseases involves problems.

We have discovered novel 4-homoisotwistane derivatives which have an anti-viral activity but which do not exhibit the side effects of amantadine. We have completed the present invention based on this discovery.

In accordance with the present invention, there are provided aminoacid amides of amine derivatives of 4-homoisotwistane (tricyclo[5.3.1.0³,⁸]undecane) represented by the following general formula (I) and acid addition salts thereof:

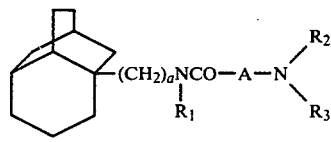

wherein a is 0 or 1, $R_1$ stands for a hydrogen atom or a lower alkyl group, A stands for a lower alkylene or lower alkylidene group, and $R_2$ and $R_3$, which can be the same or different, stand for a hydrogen atom, a lower alkyl group, a cycloalkyl group, a benzyl group or a substituted benzyl group, or they form a saturated heterocyclic ring together with the adjacent nitrogen atom.

In the general formula (I), $R_1$ stands for a hydrogen atom or a lower alkyl group. As the lower alkyl group, there can be mentioned, for example, alkyl groups having 1 to 4 carbon atoms, such as methyl, ethyl, propyl and butyl groups. It is preferred that $R_1$ is a hydrogen atom. $R_2$ and $R_3$ are defined as set forth above. As the lower alkyl group for $R_2$ and $R_3$, there can be mentioned, for example, alkyl groups having 1 to 4 carbon atoms, such as methyl, ethyl, propyl and butyl groups. As the cycloalkyl group, there can be mentioned, for example, 5-membered and 6-membered cycloalkyl groups such as cyclopentyl and cyclohexyl groups. As the substituted benzyl group, there can be mentioned, for example, groups in which the benzene ring is substituted with lower alkyl groups having 1 to 4 carbon atoms, lower alkoxy groups having 1 to 3 carbon atoms, halogen atoms such as chlorine and bromine, and a nitro group. Furthermore, $R_2$ and $R_3$ may form together with the adjacent nitrogen atom a saturated heterocyclic ring such as pyrrolidine, piperidine or morpholine ring. A stands for a lower alkylene or lower alkylidene group. For example, there can be mentioned alkylene groups having 1 to 4 carbon atoms, such as methylene, ethylene, propylene and butylene groups, and alkylidene groups having 2 to 4 carbon atoms, such as ethylidene, propylidene and butylidene groups. The term a is 0 or 1, but a compound of the general formula (I) in which a is 0 is preferred because it is easily available.

Among the compounds of the present invention, those represented by the following general formula (II) are preferred:

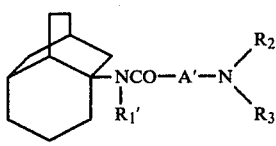

wherein $R'_1$ stands for a hydrogen atom or a methyl group, A' stands for a methylene, ethylene, propylene or ethylidene group, and $R_2$ and $R_3$ are as defined above.

Some examples of the compounds represented by the above general formula (I) are described below.

N-[3-(4-Homoisotwistyl)]-2-aminoacetamide
N-[3-(4-Homoisotwistyl)]-2-diethylaminoacetamide
N-[3-(4-Homoisotwistyl)]-2-benzylaminoacetamide
N-[3-(4-Homoisotwistyl)]-2-cyclohexylaminoacetamide
N-[3-(4-Homoisotwistyl)]-2-piperidinoacetamide
N-[3-(4-Homoisotwistyl)]-3-aminopropionamide
N-[3-(4-Homoisotwistyl)]-3-diethylaminopropionamide
N-[3-(4-Homoisotwistyl)]-3-benzylaminopropionamide
N-[3-(4-Homoisotwistyl)]-3-cyclohexylaminopropionamide
N-[3-(4-Homoisotwistyl)]-3-piperidinopropionamide
N-[3-(4-Homoisotwistyl)]-2-aminopropionamide
N-Methyl-N-[3-(4-homoisotwistyl)]-2-aminoacetamide
N-Methyl-N-[3-(4-homoisotwistyl)]-2-cyclohexylaminoacetamide
N-Methyl-N-[3-(4-homoisotwistyl)]-3-aminopropionamide N-Methyl-N-[3-(4-homoisotwistyl)]-3-cyclohex-
ylaminopropionamide The compounds of the present invention represented by the general formula (I) can be prepared by reacting a halide represented by the following general formula (III):

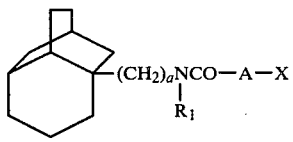

(III)

wherein a, $R_1$ and A are as defined above, and X stands for a halogen atom selected from chlorine, bromine and iodine, with an amine represented by the following general formula (IV):

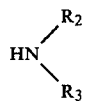

(IV)

wherein $R_2$ and $R_3$ are as defined above.

As specific examples of the amine represented by the general formula (IV), there can be mentioned ammonia, methylamine, ethylamine, propylamine, butylamine, dimethylamine, diethylamine, dipropylamine, dibutylamine, cyclohexylamine, benzylamine, methoxybenzylamine, piperidine and morpholine.

It is preferred that the reaction be carried out in an inert organic solvent. Any organic solvent inert to the reaction can be used. As organic solvents that can be advantageously used, there can be mentioned, for example, lower alcohols such as methanol, ethanol and propanol, chlorinated hydrocarbons such as methylene chloride, chloroform and carbon tetrachloride, and aromatic hydrocarbons such as benzene, toluene and xylene. It is preferred that the compound of the formula (IV) be used in an amount of about 1 to 4 moles per mole of the compound of the formula (III). The reaction is conducted at a temperature in the range of from room temperature to a temperature approximating the boiling point of the solvent used. It is preferred that the reaction be carried out at a temperature approximating the boiling point of the solvent used. The reaction is ordinarily completed within 3 to 10 hours.

A compound of the general formula (I) in which each of $R_2$ and $R_3$ is a hydrogen atom can be prepared according to the above-mentioned method, but it sometimes happens that by-products are formed when the above-mentioned method is adopted. In such a case, there can be employed a method in which a compound of the formula (III) is first reacted with potassium phthalimide to form a phthalimide derivative and the derivative is then decomposed by hydrazine or an alkali such as sodium hydroxide, potassium hydroxide or barium hydroxide, whereby the intended primary amine derivative [$R_2$=$R_3$=H in the formula (I)] can easily be prepared. According to this method, formation of by-products is remarkably reduced. In this method, potassium phthalimide is used in an amount of 1 to 2 moles, preferably 1.1 to 1.3 moles, per mole of the compound of the formula (III). As the solvent, there are employed glycols such as ethylene glycol, chlorinated hydrocarbons such as methylene chloride and chloroform, and dimethylformamide (DMF). Dimethylformamide is especially preferred because the reaction time is shortened and the yield is improved. The reaction is carried out at a temperature of 30° to 160° C., preferably 100° to 130° C. Decomposition of the phthalimide derivative is performed in an aqueous solution of an alkali at 50° to 100° C., preferably 80° to 100° C. or in an ethanol solution of hydrazine at 50° to 80° C., preferably 70° to 80° C., whereby the intended primary amine derivative [$R_2$=$R_3$=H in the formula (I)] can easily be prepared. Hydrazine is used in an amount of 1 to 3 moles, preferably 1 to 1.5 moles, per mole of the phthalimide derivative.

Furthermore, a compound of the formula (I) in which $R_2$ and $R_3$ stand for a hydrogen atom can be prepared according to a method in which a compound of the formula (I) in which $R_2$ is a hydrogen atom and $R_3$ is a benzyl or substituted benzyl group is first prepared and this compound is hydrogenolyzed. Hydrogenolysis can be carried out under conditions (catalyst, temperature and hydrogen pressure) customarily adopted in hydrogenation.

The acid addition salts of the compound of the formula (I) can easily be prepared by neutralizing the thus-obtained compound of the formula (I) with an acid. Either a mineral acid or an organic acid may be used for this neutralization. As the mineral acid, there can be mentioned, for example, hydrohalogenic acids such as hydrochloric acid, hydrobromic acid and hydroiodic acid, phosphoric acid, pyrophosphoric acid, sulfuric acid, thiosulfuric acid and boric acid. As the organic acid, there can be mentioned, for example, fatty acids such as formic acid, acetic acid, propionic acid, butyric acid, capric acid and lauric acid, saturated dibasic acids such as oxalic acid, malonic acid, succinic acid, glutaric acid and adipic acid, aliphatic hydroxyacids such as glycolic acid, malic acid, lactic acid, tartaric acid and citric acid, halogenated acetic acids such as monochloroacetic acid and monobromoacetic acid, and aromatic carboxylic acids such as benzoic acid, salicyclic acid, p-hydroxybenzoic acid, m-hydroxybenzoic acid, phthalic acid and terephthalic acid. In addition, to these carboxylic acids, there can be employed organic sulfonic acids such as methane-sulfonic acid, ethane-sulfonic acid, benzene-sulfonic acid and p-toluene-sulfonic acid. Among these acids, a hydrohalogenic acid, especially hydrochloric acid, is preferred because its handling is very easy. The acid addition salt can be prepared according to customary methods, for example, a method in which the compound of the formula (I) is neutralized by a solution containing an acid as mentioned above and the mixture is dried to the solid and a method in which an acid is added to a solution of the compound of the formula (I) in diethyl ether, chloroform, carbon tetrachloride or the like and the formed precipitate of the acid addition salt is recovered by filtration. When the acid is hydrochloric acid, it is preferred to adopt a method in which dry hydrogen chloride gas is blown into a solution of the compound of the formula (I) and the formed precipitate is recovered by filtration.

The starting halide compound of the formula (III) is prepared by reacting an amine represented by the following formula (V):

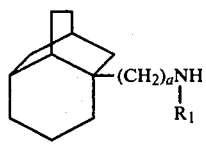

(V)

wherein a and $R_1$ are as defined above, with a halogenocarboxylic acid halide represented by the following general formula (VI):

$$X'-CO-A-X \quad (VI)$$

wherein A and X are as defined above, and X' stands for a halogen atom selected from chlorine, bromine and iodine, in the presence of a base, in an inert organic solvent. Any organic solvent inert to the reaction can be used, but there are advantageously used aromatic hydrocarbons such as benzene, toluene and xylene, linear hydrocarbon solvents such as pentane and hexane, and chlorinated hydrocarbon solvents such as methylene chloride, chloroform and carbon tetrachloride. As the base that is used for this reaction, there can be mentioned, for example, alkali metal carbonates such as sodium carbonate and potassium carbonate, and tertiary amines such as pyridine and triethylamine. It is preferred that the halogenocarboxylic acid halide be used in an amount of 1 to 1.2 moles per mole of the amine of the formula (V) and the base be used in an amount of 1 to 1.2 moles per mole of the amine of the formula (V).

The process for the formation of an amine (primary amine) of the formula (V) in which $R_1$ is a hydrogen atom is disclosed on page 536 of the above-mentioned Journal of Medicinal Chemistry, 19. The compound of the formula (V) in which $R_1$ is a lower alkyl group can be prepared by alkylating the compound of the formula (V) in which $R_1$ is a hydrogen atom with a lower alkyl halide such as methyl iodide or butyl iodide or by converting said compound to an acid amide with a lower fatty acid or its acid halide and reducing the acid amide.

The aminoacid amide compound of the present invention represented by the general formula (I) and acid addition salt thereof have an excellent anti-viral activity not only to RNA virus to also to herpes virus which is a DNA virus and they do not show any side effects on the central nervous system. Accordingly, they are very valuable as medicines for the treatment of virus-caused diseases and as anti-viral agents for animals.

The present invention will now be further described in detail by reference to the following illustrative Examples and Pharmacological Examples that by no means limit the scope of the invention.

EXAMPLE 1

(A) A solution of 2.55 g (20.1 millimoles) of 3-chloropropionyl chloride in 75 ml of dry diethyl ether was added dropwise to a mixture of 3.00 g (18.3 millimoles) of 3-amino-4-homoisotwistane, 75 ml of chloroform, 2.13 g (20.1 millimoles) of sodium carbonate and 18 ml of water, under ice cooling and agitation, over a period of 30 minutes. The mixture was further agitated for 2 hours. The aqueous layer was separated from the organic layer and was extracted with 100 ml of chloroform. The organic extract was combined with the organic layer and the mixture was washed with a saturated aqueous solution of sodium chloride and dried to remove the solvent by distillation. There was obtained 4.54 g (the yield being 97%) of N-[3-(4-homoisotwistyl)]-3-chloropropionamide in the form of white crystals.

Melting point: 84° to 86° C.

Elementary analysis values: Calculated as $C_{14}H_{22}ClNO$: C=65.75%, H=8.61%, N=5.48%, Cl=13.90%; Found: C=65.7%, H=9.0%, N=5.2%, Cl=13.2%.

IR (nujol), cm$^{-1}$: 3330, 3070, 1640, 1550.

$^1$HNMR (CDCl$_3$), δ: 1.1–2.1 (m, 17H); 2.54 (t, 2H, —COCH$_2$C$\underline{H}_2$—); 3.8 (t, 2H,—CH$_2$C$\underline{H}_2$Cl); 5.6 (bs, 1H, —N$\underline{H}$CO—).

(B) To a solution of 1.00 g (3.9 millimoles) of N-[3-(4-homoisotwistyl)]-3-chloropropionamide, obtained as described above, in 20 ml of anhydrous ethanol was added 0.86 g (11.7 millimoles) of diethylamine, and the mixture was refluxed under agitation for 3 hours. After completion of the reaction, the resulting solution was condensed and extracted with diethyl ether after addition of 100 ml of 10% hydrochloric acid. The hydrochloric acid aqueous solution was made alkaline with a 10% aqueous solution of sodium hydroxide and extracted 3 times with 40 ml of chloroform. The chloroform layer was washed with a saturated solution of sodium chloride and dried and the solvent was removed by distillation to obtain 0.19 g of the residue. The residue was dissolved in anhydrous diethyl ether and hydrogen chloride gas was blown into the solution. The formed precipitate was recovered by filtration and recrystallized from methanol to obtain 0.12 g (the yield being 9.4%) of N-[3-(4-homoisotwistyl)]-3-diethylaminopropionamide hydrochloride.

Melting point: 190°–192° C.

Elementary analysis values: Calculated as $C_{18}H_{33}ClN_2O$: C=65.75%, H=10.05%, N=8.52%, Cl=10.81%; Found: C=65.0%, H=9.9%, N=8.2%, Cl=11.0%.

IR (nujol), cm$^{-1}$: 3250, 2925, 2860, 2600, 1660, 1540, 1460.

EXAMPLE 2

To a solution of 1.00 g (3.9 millimoles) of N-[3-(4-homoisotwistyl)]-3-chloropropionamide in 20 ml of anhydrous ethanol was added 1.00 g (11.7 millimoles) of piperidine, and the mixture was refluxed under agitation for 5 hours. The post treatment was carried out in the same manner as described in section (B) of Example 1 to obtain 0.50 g (the yield being 38%) of N-[3-(4-homoisotwistyl)]-3-piperidinopropionamide hydrochloride.

Melting point: 202°–203° C.

Elementary analysis values: Calculated as $C_{19}H_{33}ClN_2O$: C=66.96%, H=9.69%, N=8.22%, Cl=10.43%; Found: C=65.9%, H=9.9%, N=7.9%, Cl=10.7%.

IR (nujol), cm$^{-1}$: 3250, 2900, 2600, 1650, 1540, 1460, 1380.

EXAMPLE 3

(A) A liquid mixture of 1.83 g (7.15 millimoles) of N-[3-(4-homoisotwistyl)]-3-chloropropionamide, 1.59 g (8.58 millimoles) of potassium phthalimide and 15 ml of dimethylformamide was refluxed under agitation for 24 hours. After cooling, 20 ml of water was added to the reaction mixture, and the mixture was extracted 3 times with 20 ml of chloroform and the combined extracts were washed with a 5% aqueous solution of sodium hydroxide and then with water. The chloroform solution was dried and condensed to obtain 2.1 g (the yield being 80%) of crude N-[3-(4-homoisotwistyl)]-3-phthalimidopropionamide in the form of a semi-solid.

IR (nujol), cm$^{-1}$: 1770, 1720, 1675, 1615.

(B) A liquid mixture of 0.91 g (2.48 millimoles) of N-[3-(4-homoisotwistyl)]-3-phthalimidopropionamide, 0.19 g (2.98 millimoles) of 80% hydrazine hydrate and 10 ml of ethanol was refluxed under agitation for 4 hours. After cooling, 4 ml of a 10% aqueous solution of hydrochloric acid was added to the reaction mixture, and the mixture was heated at 60°–70° C. under agitation for 2 hours. After cooling, the precipitated crystals were recovered by filtration and washed with a small amount of a 10% aqueous solution of hydrochloric acid. The filtrate was made alkaline with an aqueous solution of sodium hydroxide and extracted with diethyl ether. The extract was dried and condensed. The resulting residue was dissolved in 100 ml of anhydrous diethyl ether and dry hydrogen chloride gas was blown into the solution to form a white precipitate. The precipitate was recovered by filtration and recrystallized from methanol-diethyl ether to obtain 0.28 g (the yield being 42%) of very hygroscopic N-[3-(4-homoisotwistyl)]-3-aminopropionamide hydrochloride.

Elementary analysis values: Calculated as $C_{14}H_{25}ClN_2O$: C=61.64%, H=9.24%, N=10.27%, Cl=13.00%; Found: C=59.2%, H=9.1%, N=9.7%, Cl=12.8%.

IR (KBr), cm$^{-1}$: 3300, 2900, 1640, 1540, 1460.

EXAMPLE 4

(A) 1.50 g (13.3 millimoles) of 2-chloroacetyl chloride was added dropwise to a mixture of 2.00 g (12.1 millimoles) of 3-amino-4-homoisotwistane, 50 ml of chloroform, 1.40 g (13.3 millimoles) of sodium carbonate and 13 ml of water, under ice cooling and agitation, over a period of 30 minutes. The mixture was further agitated for 2 hours. The aqueous layer was separated from the organic layer and was extracted with 50 ml of chloroform. The organic extract was combined with the organic layer and the mixture was washed with a saturated aqueous solution of sodium chloride and dried to remove the solvent by distillation. There was obtained 2.1 g (the yield being 72%) of N-[3-(4-homoisotwistyl)]-2-chloroacetamide in the form of white crystals.

Melting point: 90° to 93° C.

Elementary analysis values: Calculated as $C_{13}H_{20}ClNO$: C=64.59%, H=8.34%, N=5.79%, Cl=14.66%; Found: C=64.2%, H=8.6%, N=5.6%, Cl=14.4%.

IR (nujol), cm$^{-1}$: 3330, 2925, 1640, 1550, 1640.

$^1$HNMR (CDCl$_3$), δ : 1.1–2.1 (m, 17H) 4.0 (s, 2H, —CH$_2$CH$_2$Cl) 6.4 (bs, 1H, —N$\underline{H}$CO—)

(B) To a solution of 1.20 g (4.96 millimoles) of N-[3-(4-homoisotwistyl)]-2-chloroacetamide and 0.49 g (4.46 millimoles) of cyclohexylamine in 20 ml of anhydrous ethanol was added an aqueous solution containing 82 mg (0.49 millimole) of potassium iodide and 0.42 g (4.96 millimoles) of sodium hydrogencarbonate, and the mixture was refluxed under agitation for 15 hours. After completion of the reaction, the resulting solution was condensed and extracted with diethyl ether after addition of 30 ml of 5% hydrochloric acid. The hydrochloric acid aqueous solution was made alkaline with a 10% aqueous solution of sodium hydroxide and extracted 3 times with 30 ml of chloroform. The chloroform layer was dried and concentrated to obtain 1.00 g of residue. The residue was dissolved in 100 ml of anhydrous diethyl ether and hydrogen chloride gas was blown into the solution. The formed precipitate was recovered by filtration and recrystallized from methanol-acetone to obtain 0.84 g (the yield being 52%) of N-[3-(4-homoisotwistyl)]-2-cyclohexylaminoacetamide hydrochloride.

Melting point: 223°–225° C.

Elementary analysis values: Calculated as $C_{19}H_{33}ClN_2O$: C=66.96%, H=9.69%, N=8.22%, Cl=10.42%; Found: C=65.8%, H=9.5%, N=7.9%, Cl=11.2%.

IR (nujol), cm$^{-1}$: 3200, 3050, 2900, 2600, 1670, 1560, 1470, 1450.

EXAMPLE 5

To a solution of 2.50 g (10.3 millimoles) of N-[3-(4-homoisotwistyl)]-2-chloroacetamide and 1.10 g (10.3 millimoles) of benzylamine in 40 ml of ethanol was added 20 ml of an aqueous solution containing 0.17 g (1.03 millimoles) of potassium iodide and 0.87 g (10.3 millimoles) of sodium hydrogencarbonate, and the mixture was refluxed under agitation for 6 hours. The post treatment was carried out in the same manner as described in section (B) of Example 4 to obtain 1.55 g (the yield being 43%) of N-[3-(4-homoisotwistyl)]-2-benzylaminoacetamide hydrochloride (recrystallized from methanol-acetone).

Melting point: 206°–208° C.

Elementary analysis values: Calculated as $C_{20}H_{29}ClN_2O$: C=68.86%, H=8.32%, N=8.03%, Cl=10.18%; Found: C=68.3%, H=8.4%, N=7.9%, Cl=10.0%.

IR* (neat), cm$^{-1}$: 3300, 2930, 2860, 1660, 1520, 1450.

$^1$HNMR* (CDCl$_3$), δ : 1.1–2.1 (m, 17H); 3.1 (s, 2H, —NHC$\underline{H}_2$C$_6$H$_5$); 3.7 (s, 2H, —CH$_2$C$\underline{H}_2$N—); 7.23 (s, 5H, benzene ring).

*: as measured with respect to the free amine

EXAMPLE 6

To a solution of 1.50 g (6.2 millimoles) of N-[3-(4-homoisotwistyl)]-2-chloroacetamide and 0.53 g (6.2 millimoles) of piperidine in 50 ml of ethanol was added 8 ml of an aqueous solution of 0.10 g (0.62 millimole) of potassium iodide and 0.52 g (6.2 millimoles) of sodium hydrogencarbonate, and the mixture was refluxed under agitation for 12 hours. The post treatment was carried out in the same manner as described in section (B) of Example 4 to obtain 1.05 g (the yield being 52%) of N-[3-(4-homoisotwistyl)]-2-piperidinoacetamide hydrochloride.

Melting point: 236°–240° C.

Elementary analysis values: Calculated as $C_{18}H_{31}ClN_2O$: C=66.13%, H=9.56%, N=8.57%, Cl=10.85%; Found: C=66.0%, H=9.6%, N=8.5%, Cl=10.7%.

IR (nujol), cm$^{-1}$: 3160, 3030, 2900, 2850, 1670, 1550, 1450.

EXAMPLE 7

(A) A liquid mixture of 1.50 g (6.2 millimoles) of N-[3-(4-homoisotwistyl)]-2-chloroacetamide, 1.38 g (7.4 millimoles) of potassium phthalimide and 15 ml of dimethylformamide was refluxed under agitation for 12 hours. After cooling in air, 20 ml of water was added to the reaction mixture, and the mixture was extracted 3 times with 20 ml of chloroform and the extract was washed with a 5% aqueous solution of sodium hydroxide and then with water. The chloroform solution was dried and condensed to obtain 2.00 g (the yield being 92%) of crude N-[3-(4-homoisotwistyl)]-2-phthalimidoacetamide in the form a semi-solid.

IR (nujol), cm$^{-1}$: 1775, 1725, 1675, 1615.

(B) A liquid mixture of 1.37 g (3.89 millimoles) of N-[3-(4-homoisotwistyl)]-2-phthalimidoacetamide, 0.29 g (4.66 millimoles) of 80% hydrazine hydrate and 10 ml of ethanol was refluxed under agitation for 4 hours. The post treatment was carried out in the same manner as in section (B) of Example 3 to obtain 0.34 g (the yield being 34%) of N-[3-(4-homoisotwistyl)]-2-aminoacetamide hydrochloride.

Elementary analysis values: Calculated as $C_{13}H_{23}ClN_2O$: C=60.34%, H=8.96%, N=10.82%, Cl=13.70%; Found: C=59.8%, H=9.2%, N=10.5%, Cl=12.8%.

IR (KBr), cm$^{-1}$: 3250, 2930, 2850, 2650, 1660, 1560, 1530.

EXAMPLE 8

(A) 3-Methylamino-4-homoisotwistane was reacted with 2-chloroacetyl chloride under the same conditions as described in section (A) of Example 4 to obtain N-methyl-N-[3-(4-homoisotwistyl)]-2-chloroacetamide in a yield of 72%.

Elementary analysis values: Calculated as $C_{14}H_{22}ClNO$: C=65.74%, H=8.67%, N=5.48%, Cl=13.86%; Found: C=65.5%, H=8.9%, N=5.3%, Cl=13.3%.

IR (nujol), cm$^{-1}$: 2900, 1660, 1460, 1380, 1270, 795.

$^1$HNMR (CDCl$_3$), δ: 1.1–2.1 (m, 17H); 3.0 (s, 3H); 4.1 (s, 2H).

(B) N-methyl-N-[3-(4-homoisotwistyl)]-2-chloroacetamide was reacted with potassium phthalimide under the same conditions as described in section (A) of Example 7 to obtain N-methyl-N-[3-(4-homoisotwistyl)]-2-phthalimidoacetamide in the form of white crystals in a yield of 78%.

Melting point: 198°–200° C.

Elementary analysis values: Calculated as $C_{22}H_{26}N_2O_3$: C=72.10%, H=7.15%, N=7.65%; Found: C=72.0%, H=7.4%, N=7.5%.

IR (nujol), cm$^{-1}$: 2900, 1775, 1720, 1655, 1615.

NHMR (CDCl$_3$), δ: 1.2–2.2 (m, 17H); 3.0 (s, 3H, —N—CH$_3$); 4.45 (s, 2H, —CO CH$_2$N—); 7.8 (4H, benzene ring).

(C) N-methyl-N-[3-(4-homoisotwistyl)]-2-phthalimidoacetamide was reacted with 80% hydrazine hydrate under the same conditions as described in section (B) of Example 7 to split off the phthalyl group. By neutralization with hydrogen chloride gas, there was obtained N-methyl-N-[3-(4-homoisotwistyl)]-2-aminoacetamide hydrochloride in a yield of 73%.

Melting point (recrystallized from methanol-acetone): 205°–207° C.

Elementary analysis values: Calculated as $C_{13}H_{25}ClN_2O$: C=61.65%, H=9.17%, N=10.27%, Cl=13.02%; Found: C=60.0%, H=9.5%, N=10.0%, Cl=13.1%.

IR (KBr), cm$^{-1}$: 3300–2500, 2200, 1650, 1590, 1550, 1480, 1410, 1360, 1330, 1290, 1170, 1140, 1110, 1070, 1030, 920.

EXAMPLE 9

In the same manner as described in Example 8, N-[3-(4-homoisotwistyl)]-3-chloropropionamide was converted to a phthalimide derivative and it was further converted to an amine derivative by 80% hydrazide hydrate to obtain N-[3-(4-homoisotwistyl)]-3-aminopropionamide hydrochloride in a yield of 32%. This compound was very hygroscopic.

Elementary analysis values: Calculated as $C_{15}H_{27}ClN_2O$: C=61.65%, H=9.17%, N=10.27%, Cl=13.02% Found: C=59.2%, H=9.8%, N=9.2%, Cl=12.5%.

IR (KBr), cm$^{-1}$: 3500–3200, 2900, 1670, 1550, 1460, 1120;

MS, m/e (relative intensity): 236 (11), 149 (11), 67 (9), 44 (100).

Pharmacological Example 1

The activity of the compounds named below for controlling haloperidol-induced catalepsy was examined to determine the activity of the compounds on the central nervous system. The results obtained are shown in Table 1.

TABLE 1

| | Anti-Catalepsy Activity | |
|---|---|---|
| Compound | Amount Administered (mg/Kg) | Number of Influenced Animals/Number of Tested Animals |
| N-[3-(4-homoiso-twistvl)]-2-amino-acetamide hydrochloride | 100 | 0/5 |
| Amantadine (1-amino-adamantane hydrochloride) | 100 | 4/5 |
| 3-amino-4-homo-isotwistane hydrochloride | 100 | 5/5 |

Test Procedures

Haloperidol was subcutaneously administered to mice to induce catalepsy. When 3 hours had passed from administration of haloperidol, the compound was abdominally administered, and after 1 hour, the presence or absence of the catalepsy was examined. The front legs of the mouse were hung on a stainless steel rod having a diameter of 3mm, which was kept horizontal at a height of 3.5 cm, and when the time of duration of this posture was less than 30 seconds, it was judged that the catalepsy was controlled and the mouse was influenced by the compound.

As will be apparent from the results shown in Table 1, the compound of the present invention exhibits a much lower side effect than Amantadine with respect to the action on the central nervous system.

Pharmacological Example 2

The anti-viral activity was tested in vivo by using mice infected with mouse-tamed A/PR/8/34 (HONI) influenza virus. The results obtained are shown in Table 2.

TABLE 2

| | Anti-Influenzal Action | | |
|---|---|---|---|
| Compound Tested | Amount Administered (mg/Kg) | Survival Ratio | LLS Value |
| N-[3-(4-homoiso-twistyl)]-2-amino-acetamide hydrochloride | 15 | 4/10 | 4.30 |
| 3-amino-4-homo-isotwistane hydrochloride | 15 | 6/10 | 4.00 |

TABLE 2-continued

| | Anti-Influenzal Action | | |
|---|---|---|---|
| Compound Tested | Amount Administered (mg/Kg) | Survival Ratio | LLS Value |
| Amantadine | 25 | 7/10 | 4.10 |
| Amantadine | 10 | 7/10 | 4.30 |
| Control | — | 1/9 | 4.80 |

Virus

Mouse-tamed A/PR/8/34 (HONI) influenza virus.

Animal

Male mice of the dd system, 3 weeks old, body weight of 12–13 g.

Infection with virus

Method of Kashiwagi et al. [Journal of Medicine of Fukuoka, 65 (3), 157–171 (1974)]

Administration of compounds

The test compound was dissolved in physiological saline solution, and 0.1 ml of the solution was subcutaneously injected. The concentration of the compound was adjusted so that the amount shown in Table 2 was administered to the mouse having a body weight of 12 g. Administration was continued in the same amount irrespective of the change of the body weight. On the day when infection was performed, the solution was administered 3 times, that is, 2 hours before the infection, 2 hours after the infection and 6 hours after the infection, and the administration was conducted at intervals of 12 hours for subsequent 6 days.

Lung Lesion score (LLS value)

The mice that died during the experiment were anatomized when they died and the surviving mice were killed on the 7th day and anatomized. The LLS value was determined according to the method of Tani et al. [Journal of Medicine of Fukuoka, 58 (9), 801–815 (1967)]. Each of the LLS values in Table 2 is an average value for the total mice tested.

Survival ratio:

The survival ratio is expressed in terms of the ratio of the number of mice that survived to the 7th day to the total number of mice tested.

The embodiments of the invention in which an exclusive property or privilege is claimed are defined as follows:

1. A compound having the formula

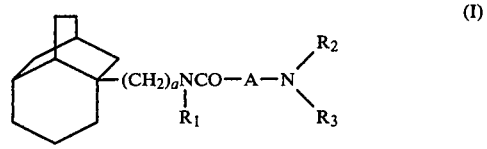

(I)

wherein a is 0 or 1, $R_1$ is hydrogen or lower alkyl, A is lower alkylene or lower alkylidene, and $R_2$ and $R_3$, which can be the same or different, are hydrogen, lower alkyl, cycloalkyl, benzyl, benzyl substituted on the ring with alkyl having 1 to 4 carbon atoms, alkoxy having 1 to 3 carbon atoms, chloro, bromo or nitro, or

forms a saturated heterocyclic ring selected from the group consisting of pyrrolidine, piperidine and morpholine, and pharmacologically acceptable acid addition salts thereof.

2. A compound as set forth in claim 1 wherein a is 0.

3. A compound as set forth in claim 1 wherein $R_1$ is hydrogen.

4. A compound as set forth in claim 1 wherein the acid is an organic acid.

5. A compound as set forth in claim 1 wherein the acid is a mineral acid.

6. A compound as set forth in claim 5 wherein the mineral acid is a hydrohalogenic acid.

7. A pharmaceutical composition which comprises as an active ingredient a pharmaceutically effective amount of a compound as claimed in claim 1 and at least one pharmaceutically acceptable carrier or diluent.

8. A compound as set forth in claim 1 in which said lower alkyls have 1 to 4 carbon atoms; said cycloalkyl has 5 or 6 carbon atoms; said alkylene group has from 1 to 4 carbon atoms; and said alkylidene group has from 2 to 4 carbon atoms.

9. A compound as set forth in claim 1, namely N-[3-(4-homoisotwistyl)]-2-aminoacetamide hydrochloride.

* * * * *